United States Patent [19]
Korn

[11] 4,212,638
[45] Jul. 15, 1980

[54] CONVERTIBLE LIGHT WIRE-RECTANGULAR WIRE ORTHODONTIC APPLIANCE SYSTEM

[76] Inventor: Marcel Korn, 502 Lindell Ave., Leominster, Mass. 01453

[21] Appl. No.: 958,959

[22] Filed: Nov. 9, 1978

[51] Int. Cl.² .............................................. A61C 3/00
[52] U.S. Cl. ........................................... 433/8; 433/16
[58] Field of Search ........................... 32/14 A; 433/8

[56] References Cited
U.S. PATENT DOCUMENTS

| | | | |
|---|---|---|---|
| 1,323,141 | 11/1919 | Young | 32/14 A |
| 2,908,974 | 10/1959 | Stifter | 32/14 A |
| 3,128,553 | 4/1964 | Broussard | 32/14 A |
| 3,134,171 | 5/1964 | Kessler | 32/14 A |
| 3,163,933 | 1/1965 | Begg | 32/14 A |
| 3,178,822 | 4/1965 | Fogel et al. | 32/14 A |

Primary Examiner—Robert Peshock

[57] ABSTRACT

This invention is that of a combination light wire—rectangular wire orthodontic appliance system which provides the practitioner with a means for employing both treatment methods without the necessity of changing brackets during the treatment. A standard bracket is provided which is adapted to receive an archwire in an archwire receiving channel opening onto the gingival surface of the bracket. The archwire is secured to the bracket by means of a lock pin positioned in the lock pin—insert receiving slot of the bracket. This combination provides a light wire appliance.

The bracket is also adapted to receive a detachably mountable insert in the lock pin—insert receiving slot. The insert has a rectangular archwire slot open on its buccal or labial surface which is adapted to receive a rectangular archwire. This combination is a rectangular wire appliance. The detachable insert is provided with an archwire receiving slot having varying axial height on the insert's body or various degrees of torque and/or angulation. These detachable inserts eliminate or reduce wire bending to effect tooth movement.

16 Claims, 19 Drawing Figures

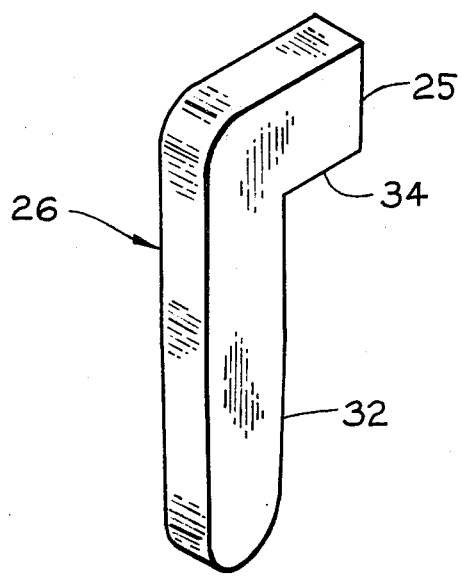
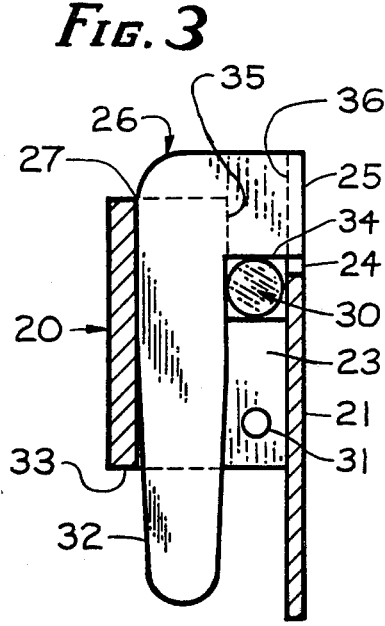
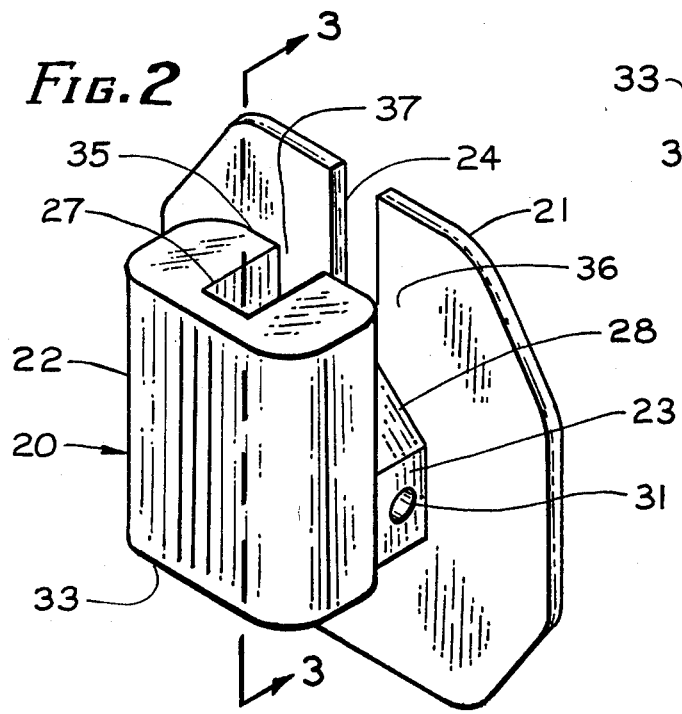

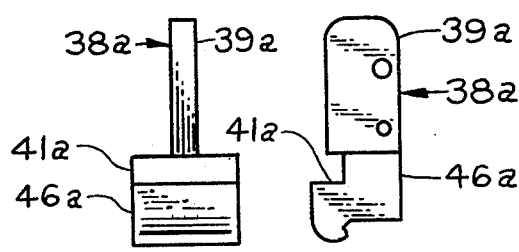
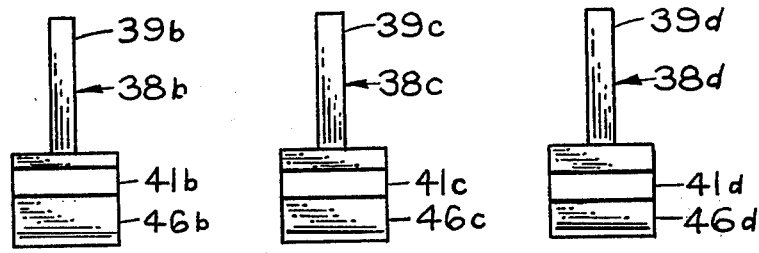
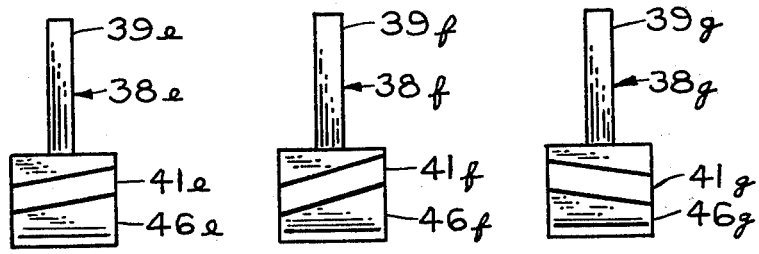
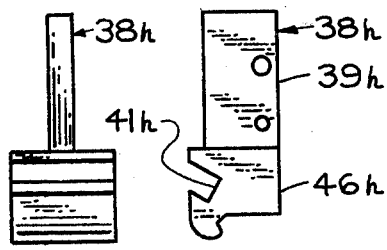
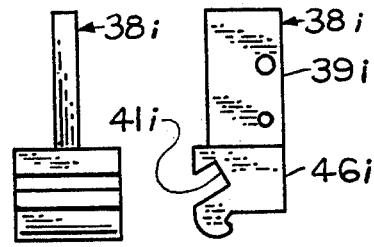

CONVERTIBLE LIGHT WIRE-RECTANGULAR WIRE ORTHODONTIC APPLIANCE SYSTEM

BACKGROUND OF THE PRIOR ART

The practice of orthodontics involves the correction of dental irregularities and malocclusions by the application of forces to the teeth. The orthodontist applies corrective forces to the teeth requiring repositioning by attaching orthodontic appliances to them. These appliances are then connected to each other by an archwire made of a spring-like metal e.g., stainless steel. The orthodontist controls the amount and direction of the forces required to effect a repositioning of the teeth by selective bending of the archwire. This invention is directed to a more selective and precise method of applying such corrective forces and an appliance system designed to implement this improved treatment method.

Current standard orthodontic treatment methods employing fixed orthodontic appliances can for the most part be divided into two broad categories i.e., the light wire method and rectangular wire (or edgewise) method. Each of these methods has its advantages and its disadvantages. The improved orthodontic appliance system of this invention allows the practitioner to utilize the advantages of both and to avoid the disadvantages inherent in each method.

The light wire method involves effecting tooth movement by tipping and torquing the tooth into a new position. In the light wire method, an appliance, attached to a tooth, is connected to an archwire at what can be described as a point contact. Corrective force is applied to the tooth through the archwire, but because of the point contact connection between the archwire and the tooth, it is free to rotate and tip. This rather loose connection allows the tooth to move easily and large changes in tooth position can be accomplished by the use of light forces. However, since the tooth is relatively free to move, it is difficult to precisely control its final position.

The rectangular wire method uses a more rigid system to effect tooth movement. A rectangular archwire is positioned in a rectangular slot in an appliance that has been attached to a tooth. The degree of freedom of the tooth to move in any direction is limited because of the rigid connection formed by the rectangular archwire in the rectangular archwire receiving slot. A tooth so attached must move along or with the archwire and precise repositioning is possible. However, since the connection between the appliance and the archwire is rigid and extensive, large frictional forces are encountered and therefore higher forces must be used to accomplish a particular tooth movement. Generally a longer treatment time is required to effect large tooth movement by this method than by the light wire method.

Various attempts have been made in the past to design orthodontic appliances that are capable of being utilized to effect both methods of treatment. U.S. Pat. Nos. 3,163,933 and 3,178,822 describe combination one-piece orthodontic appliances having the capability of being used in either the light wire or rectangular wire method. These devices have enjoyed limited success perhaps because of their design or lack of flexibility.

U.S. Pat. No. 3,128,553 describes an orthodontic appliance with an interchangeable element that permits the orthodontist to eliminate some of the control problems inherent in the light wire treatment method. The appliance in a first configuration is a standard light wire unit. As treatment progresses, an auxiliary element having laterally projecting wing portions is insertable in the appliance and the tendency for the tooth to rotate about its vertical (gingival-occlusal) axis is reduced by the extending wings.

Various other attempts have been made in the past to provide a less empirical approach to orthodontic treatment which is in part an art centering about the orthodontist's skill and speed in constructing arch-wires with the proper force-producing bends. One such attempt is the so called straight-wire technique. This is a modified rectangular wire system wherein the orthodontist first makes a model of the patient's dental arch. Then using this model, he selects certain rectangular wire appliances having what he considers to be the proper amounts of torque and/or angulation to effect the repositioning of the teeth. Still using the model of the patient's dental arch, he welds the selected appliances on bands at predetermined positions based on his study of the model. These bands are then positioned on the model, an archwire is constructed with predetermined bends and then the whole assembly is transferred to the patient's teeth.

U.S. Pat. No. 2,908,974 describes a rectangular wire appliance in which the archwire is attached to a tooth by means of a two-piece unit having a female member attached to the tooth and detachable male member having an archwire receiving slot. The male member of this device can be constructed with different degrees of angulation or torque and they can be changed as treatment progresses to effect positioning of the teeth with minimal wire bending. This device does not have the capability of being used in the light wire treatment method and its design makes it difficult to effect a rigid connection between the female member and the male member.

Although the straight wire treatment method can be considered a more precise method than the conventional rectangular wire system, it is time consuming and it is not easily modified. One skilled in the art will readily appreciate the advantages of my invention hereinafter described since it provides all the advantages of the rectangular wire or straight wire methods with the increased capability for quick modification as treatment progresses, and the advantage of light wire treatment capability.

Another not so apparent advantage of my invention is that it provides a practical and safe means for an orthodontist trained in the light wire treatment method to practice the rectangular wire method without radically diverting from his primary skill; the converse, of course, being applicable to one having his basic training in rectangular wire treatment method.

SUMMARY OF THE INVENTION

This invention is directed to a convertible light wire—rectangular wire appliance system that may be used in either the light wire treatment method or the rectangular wire method. The description is written in terms of applying the appliance to the maxillary arch, however, proper reversing of description terms (gingival-occlusal) where appropriate, will be readily apparent to those skilled in the art when the appliance is attached to the mandibular arch. This appliance system comprises four principal parts: (1) a bracket designed to be attached to a tooth and receive an archwire; (2) a lock pin designed to hold the archwire to the bracket; (3) an insert having a rectangular wire retaining means and adapted to be detachably mounted to the bracket and (4) locking means for mounting the insert to the bracket.

The bracket and lock pin parts of the improved orthodontic appliance system of this invention are used in combination when practicing the light wire treatment method. The bracket is attached to a tooth usually by welding it to a tooth band which is cemented to the tooth. Extending horizontally across the bracket is a three-sided, archwire receiving channel open on the gingival surface of the bracket and adapted to receive an archwire. A lock pin-insert receiving slot extends vertically through the bracket and is adapted to receive the lock pin. The archwire is held in the channel by placing the archwire in the channel, positioning the lock pin in the lock pin-insert receiving slot and bending the lock pin over the occlusal surface of the bracket.

In practicing the rectangular wire treatment method, the bracket, the insert and the insert locking means are used in combination. The bracket is attached to a tooth. The insert is placed in the lock pin-insert receiving slot of the bracket and detachably mounted to the bracket by locking means generally a dowel type pin. The insert has a three-sided, rectangular archwire receiving slot open on the buccal or labial surface of the insert and extending horizontally across the insert in the mesial-distal direction. The rectangular archwire used in this treatment method is secured to the insert by the use of a ligature wire. The insert may be provided with a rectangular archwire receiving slot having various degrees of angulation, or torque and it may be positioned at different axial heights on the body of the insert. The detachable inserts of the appliance system allow the orthodontist to select an insert with the proper combination of torque, angulation or axial height to exert differential forces on the tooth with a minimum of wire bending and these inserts may be changed as treatment progresses to effect exact positioning of a tooth without a wire or bracket change.

The convertible appliance system of this invention allows the practitioner to use the light wire and/or the rectangular wire treatment method in correcting a tooth's position at any stage of the patient's treatment. It is readily apparent that the orthodontist can use the light wire method on one or a number of teeth while simultaneously using the rectangular method on others with the convertible appliance system of this invention. Other advantages of this invention will become apparent on reading the following description of the preferred embodiments.

BRIEF DESCRIPTION OF THE DRAWINGS

FIG. 1 is a perspective view of a lock pin.
FIG. 2 is a perspective view of the bracket.
FIG. 3 is a sectional side view through the plane 3—3 of FIG. 2 showing an assembled light wire appliance comprising the bracket, the lock pin and a round archwire.

FIG. 8a and FIG. 8b are a front and side view respectively of a modified insert.
FIG. 9a–9e are front views of modified inserts in which the archwire receiving slots are positioned at different axial heights on the insert.
FIGS. 10a–10e are front views of modified inserts showing different degrees of angulation.
FIG. 11a–FIG. 12b are front and side views of two modified inserts showing different degrees of torque.

DESCRIPTION OF THE PREFERRED EMBODIMENTS

Figure 4:
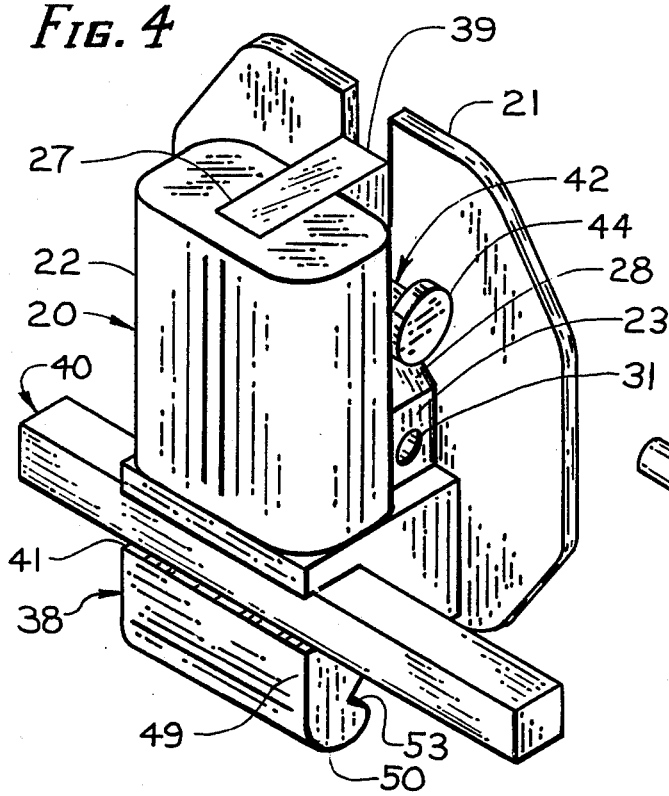
FIG. 4 is a perspective view of the bracket, the insert and a rectangular archwire assembled as a rectangular wire appliance.

FIG. 1 to FIG. 12b illustrate the component parts of this invention which provide an orthodontist with a convertible light wire-rectangular wire appliance system for correcting tooth position. FIG. 1–FIG. 3 of the drawings illustrate component parts of this invention and their assembly into an appliance adapted for use in the light wire treatment method. FIG. 4–FIG. 7 of the drawings illustrate component parts of this invention and their assembly into an appliance adapted for use in the rectangular treatment method. FIG. 8a through FIG. 12b illustrate modified forms of the insert of this invention adapted for use in assembling a unit for use in the rectangular wire treatment method.

Referring first to FIG. 1–FIG. 3 which illustrate component parts of this invention and their assembly into a light wire appliance. FIG. 2 illustrates a bracket 20 in perspective view. The bracket 20 is attached to a tooth (not shown) by welding or soldering the flange 21 of a bracket 20 to a generally circular tooth band (not shown) which is in turn placed over and cemented to the tooth under treatment. The bracket 20 may alternatively be attached directly to the tooth by direct bonding of the flange 21 to the tooth with adhesive.

The bracket 20 is a three member structure comprising a body 22 and a flange 21 joined to each other by an intermediate section 23. The bracket 20 may be constructed as a one piece unit by casting, molding or machining techniques. Preferably, it is made from stainless steel or an equivalent inert metal or plastic. The body 22 and the intermediate section 23 however, may be made as one unit, the flange 21 as another and the two assembled.

A flange slot 24 extends downwardly through the upper portion of the flange 21. The flange slot 24 is designed to receive the face portion 25 of the lock pin 26 shown in perspective view in FIG. 1 when the lock pin 26 and bracket 20 are assembled. The vertical extent of the flange slot 24 is greater than the vertical extent of the face portion 25 in order for the lock pin 26 to seat in the bracket 20.

Referring to FIG. 2 and FIG. 3, a lock pin-insert receiving slot 27 is shown extending vertically through the body 22 and the intermediate section 23 of bracket 20. The upper surfaces 28 of the intermediate section 23 of bracket 20 are inclined inwardly and upwardly to define a pivot surface 29 upon which the archwire 30 rests when the appliance is assembled. The purpose of inclining the upper surfaces 28 of the intermediate section 23 inwardly and upwardly is to present a reduced area, designated as a pivot surface 29. The term pivot surface as used in this description is meant to define the upper most surfaces formed by the adjacent upwardly and inwardly inclined surfaces 28 of the intermediate section 23 of the bracket 20. The pivot surface 29 provides a fulcrum for the archwire 30 so that the tooth under treatment is free to move about that surface and provide a point of reduced area between the bracket and the archwire to minimize frictional drag between the bracket 20 and the archwire 30.

The intermediate section 23 of the bracket 20 has a ligature wire hole 31 extending horizontally through the intermediate section 23. The ligature wire hole 31 can be used in the light wire treatment method to provide an attachment point for elastics or other auxiliary devices such as upright springs or torquing auxiliaries.

FIG. 3 is a section view of the appliance along the plane 3—3 of FIG. 2 showing the lock pin 26 of FIG. 1 in assembled relationship with the bracket 20 and the archwire 30. The lock pin 26 is secured by crimping or bending (not shown) the leg portion 32 of the lock pin 26 across the bottom 33 of the bracket 20.

As can be seen from FIGS. 2 and 3, the pivot surface 29 of the intermediate section 23, the upper interior surface 35 of body 22 and the opposing surface 36 of the flange 21 define a horizontally extending channel 37 adapted to receive the archwire 30. The archwire 30 is held in position in the channel 37 and urged against the pivot surface 29 by the lower surface 34 of the lock pin 26 when the leg 32 of the lock pin 26 is crimped across the base 33 of the bracket 20.

Figure 5:
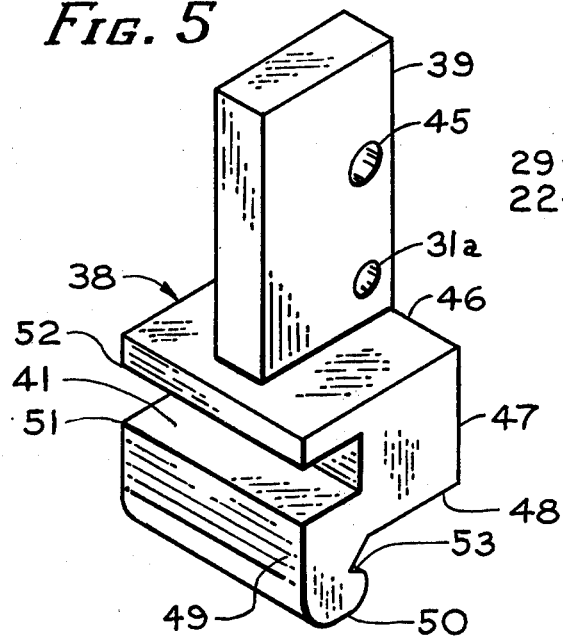
FIG. 5 is a perspective view of the insert.

Now referring to FIG. 4–FIG. 7, all perspective views, which illustrate other component parts of the invention and their assembly as a rectangular wire appliance. FIG. 5 illustrates an insert 38. The insert 38 is adapted to receive a rectangular archwire 40 when it is assembled with the bracket 20 as shown in FIG. 4. The insert 38 is detachably mountable to the bracket 20 by a locking means shown in FIG. 6 as a dowel 42.

Figure 6:
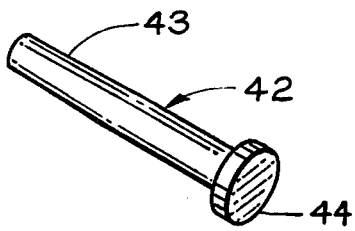
FIG. 6 is a perspective view of the dowel.

The insert 38 as shown in FIG. 5 comprises a post 39 and a base 46. The post 39 is adapted to be positioned in the lock pin-insert receiving slot 27 of the bracket 20. Located in the post 39 is a dowel hole 45 adapted to receive a dowel 42. The dowel 42 as shown in FIG. 6 comprises a shaft 43 and a head portion 44. The shaft 43 is tapered to facilitate ease of placement of the dowel 42 when securing the insert 38 to the bracket 20.

Figure 7:
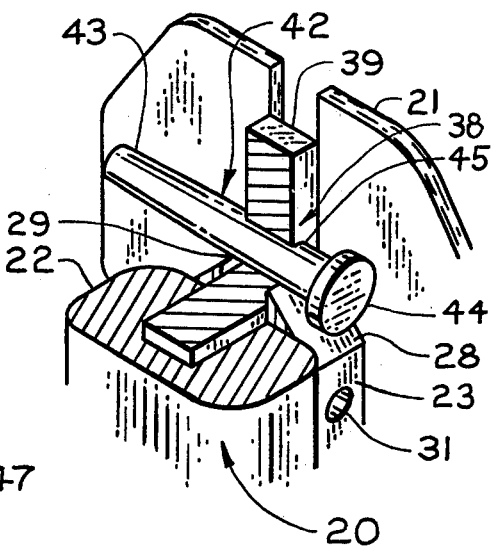
FIG. 7 is a partial sectional view of FIG. 4 showing the assembled rectangular wire appliance and illustrating how the dowel locks the insert to the bracket.

The assembled relationship of the insert 38, the bracket 20 and the dowel 42 is best seen in the sectional view, FIG. 7. The tapered dowel is passed over the pivot surface 29 of the bracket 20 and through the dowel hole 45 of the insert 38 so as to lock the insert 38 to the bracket 20. The shaft 43 of the dowel 42 is crimped over the intermediate surface 23 of the bracket 20 to fasten the dowel 42 in position.

In order to provide a more rigid assembly of the insert 38 to the bracket 20, the dowel 42 may be provided with a flat on one side of the shaft 43 to provide more contact area between the shaft 43 and the pivot surface 29 of bracket 20. Other locking devices such as those of a pop-rivet or cotter key type design may be used to effect locking of the insert 39 to the bracket 20.

Similarily it is within the scope of my invention to construct an insert so as to enable one to adapt it for use with standard light wire bracket. For instance, the insert can be a multi-post element adapted to be assembled to a conventional light wire bracket.

Referring again to FIG. 5, located in the post 39 of the insert 38 is a ligature wire hole 31a. Ligature wire 31a is positioned in the post 39 so as to align with the ligature hole 31 of the bracket 20 when the bracket 20 and the insert 38 are assembled. The ligature wire (not shown) is used to hold the rectangular archwire 40 in the rectangular archwire receiving slot 41 of insert 38. The surfaces 51 and 52 defining the lower and upper surfaces respectively of the rectangular archwire receiving slot 41. The ligature wire is secured in place over the rectangular archwire 40 by looping it over the wing portion of base 50 and into the groove 53 provided between the buccal or labial surface 49 and the lingual surface 47 of insert 38.

The grove 53 is best seen in FIG. 4 at the buccal or labial end of the lower surface 48 of the insert 38. One end of the ligature wire is passed over the rectangular archwire 40 and through the ligature holes 31 and 31a. The other end of the ligature wire is similarly passed over the rectangular archwire 40 and secured to the first end of the ligature wire by twisting the two portions together.

Preferably, the insert 38 is made of stainless steel or an equivalent inert substance and the dowel 42 is made of ductile tough material such as brass.

FIGS. 8a and 8b illustrate a modified form of the insert 38a. In this embodiment, the lower surface 33 of bracket 20 provides the upper surface of the rectangular archwire receiving slot 41a. The top of post 39a of insert 38a is rounded in this embodiment to facilitate ease of placement in the bracket 20. Although not shown, the top of post 39a may be provided with a groove extending across its top in a mesial-distal direction. This groove can be used as an attachment point for an elastic.

FIGS. 9a-9c illustrate modified inserts 38b-38d in which the rectangular archwire receiving slots 41b-41d are at different axial heights on the bases 46b-46d of the inserts 38b-38d. These inserts 38b-38d provide means for compensating for tooth height or size and reduce the need to bend the rectangular archwire 40 when leveling teeth of different axial heights.

FIGS. 10a-10c illustrate inserts 38e-38g having rectangular archwire receiving slots 41e-41g with various degrees of angulation to the mesial-distal plane (perpendicular to the gingival-occlusal axis) of the teeth. Again, the need to bend the rectangular archwire is eliminated or reduced by selection of the proper insert when movement is desired in the mesial-distal direction.

FIG. 11a-FIG. 12b illustrate inserts 38h-38i having rectangular archwire receiving slots 41h-41i with various degrees of torque to the gingival-occlusal axis of the teeth. Selection of the proper insert allows the application of the proper differential force to a particular tooth without the need to bend the archwire.

It is to be understood that a single insert can be constructed with a combination of axial height, angulation or torque features in order to effect simultaneous tooth movement in several planes.

In summary, the foregoing text describes a convertible light wire-rectangular wire appliance system for correcting tooth position. The orthodontist is provided with a standard bracket that can be secured to the patient's teeth and by choice of a lock pin or an insert herebefore described, effect tooth movement by the light wire or the rectangular wire method without the necessity of removing the brackets from the patient's teeth in order to change from one method to the other. Similarly, the detachable inserts of my system provide a means for precisely controlling tooth movement without the necessity of archwire bending, archwire replacement or bracket replacement.

The ability to move from one treatment method to another and the precise control of tooth movement provided by this appliance system will result in faster treatment time both in terms of the orthodontist's working time and the duration of treatment. Since my appliance system also avoids the use of high differential forces, better and less painful treatment will result.

I envision that in practice my convertible light wire-rectangular wire orthodontic appliance system will be furnished to the practitioner in a kit consisting of bracket and pin combinations and enumerable combinations of rectangular wire inserts of various thickness, heights, angulations, widths and torques. The practitioner will then reorder specific rectangular wire inserts, brackets and pins as needed in the conduct of his practice.

Although my invention has been described in terms of specific embodiments which are set forth in considerable detail, it should be understood that this was done for illustrative purposes only and that the invention is not necessarily limited thereto since alternative embodiments will become apparent to those skilled in the art in view of this disclosure. For instance, I have described the archwire receiving slot of the insert of my invention as a rectangular archwire receiving slot, this particular geometric form of this slot and the archwire may be changed without losing the rigid connection achieved by the rectangular configuration. Accordingly this and other modifications are contemplated which can be made without departing from the spirit of the described invention.

What I claim is:

1. A convertible light wire-rectangular wire orthodontic appliance system adapted for use with an archwire comprising:
   A. A bracket adapted to be attached to a tooth, (and receive an archwire in) said bracket having a channel extending horizontally across the upper surface of said bracket in the mesial-distal direction, said channel being open onto said upper surface and adapted to receive an archwire, said bracket having lock pin-insert receiving means adapted to receive either a lock pin (and) or an insert;
   B. a lock pin, said lock pin being adapted to be positioned in said lock pin-insert receiving means and adapted to secure an archwire in said channel when said bracket and lock pin are used in the light wire, orthodontic treatment method;
   C. an insert, said insert having an archwire receiving slot extending generally horizontally across said insert in the mesial-distal direction and open onto the buccal or labial surface of said insert, said insert being adapted to be positioned in said lock pin-insert receiving means when said bracket and said insert are used in the rectangular wire orthodontic treatment method;
   D. locking means for detachably mounting said insert to said bracket;
wherein said bracket and said lock pin are adapted to be assembled into a light wire orthodontic appliance and wherein said bracket, said insert, and said locking means are adapted to be assembled into a rectangular wire orthodontic appliance.

2. The convertible light wire-rectangular wire orthodontic appliance system of claim 1 wherein said bracket is a three member structure comprising a body and a flange connected by an intermediate section and wherein said lock pin-insert receiving means is a slot extending vertically through said body and said intermediate section of said bracket.

3. The convertible light wire-rectangular wire orthodontic appliance system of claim 2 wherein the upper surfaces of said intermediate section are inclined upwardly and inwardly to define a pivot surface.

4. The convertible light wire-rectangular wire orthodontic appliance of claim 2 or 3 wherein said archwire receiving slot of said insert is inclined at an angle to at least one axis of said insert.

5. The convertible light wire-rectangular wire orthodontic appliance system of claim 1 wherein said insert comprises a base and a post, said post being adapted to be positioned in said lock pin-insert receiving means for detachable mounting to said bracket.

6. The convertible light wire-rectangular wire orthodontic appliance system of claim 5 wherein said archwire receiving slot of said insert is inclined at an angle to at least one axis of said insert.

7. The convertible light wire-rectangular wire orthodontic appliance system of claim 5 wherein said archwire receiving slot of said insert is inclined to the mesial-distal plane of said insert to provide a predetermined amount of angulation.

8. The convertible light wire-rectangular wire orthodontic appliance system of claim 5 wherein said archwire receiving slot of said insert is inclined to the gingival-occlusal axis of said insert to provide a predetermined amount of torque.

9. An orthodontic appliance adapted for use with an archwire comprising a bracket adapted to be attached to a tooth, said bracket having a channel extending horizontally across the upper surface of said bracket in the mesial-distal direction and open onto said upper surface, said bracket having a lock pin-insert receiving means and an insert comprising a post and a base, said post being positioned in said lock pin-insert receiving means and said insert being detachably mounted to said bracket by locking means, said insert having an archwire receiving slot extending generally horizontally across the base portion of said insert and open onto the buccal or labial surface of said insert.

10. An orthodontic appliance according to claim 9 wherein said bracket is a three member structure comprising a body and a flange connected by an intermediate section and wherein said lock pin-insert receiving means is a slot extending vertically through said body and said intermediate section of said bracket.

11. An orthodontic appliance according to claim 9 wherein said archwire receiving slot of said insert is inclined at an angle to at least one axis of said insert.

12. An archwire receiving insert adapted to be detachably mountable to a bracket, said bracket being adapted to be attached to a tooth, said bracket having an insert receiving slot adapted to receive said insert, wherein said insert comprises a base and a post, said post portion comprising a vertical extending member with said base portion being located at one end of said post, said base having an archwire receiving slot extending generally horizontally across said base in the mesial-distal direction and open onto the buccal or labial surface of said base, said post being adapted to be positioned in said insert receiving slot of said bracket and detachably mountable to said bracket by removeable locking means.

13. An archwire receiving insert according to claim 12 wherein said archwire receiving slot is inclined at an angle to at least one axis of said insert.

14. An archwire receiving insert according to claim 12 wherein said archwire receiving slot is inclined to the mesial-distal plane of said insert to provide a predetermined amount of angulation.

15. An archwire receiving insert according to claim 12 wherein said archwire receiving slot is inclined to the gingival-occlusal axis of said insert to provide a predetermined amount of torque.

16. An archwire receiving insert according to claim 12 wherein said archwire receiving slot is inclined to the mesial-distal plane of said insert to provide a predetermined amount of angulation and inclined to the gingival-occlusal axis of said insert to provide a predetermined amount of torque.

* * * * *

UNITED STATES PATENT AND TRADEMARK OFFICE
CERTIFICATE OF CORRECTION

PATENT NO. : 4,212,638
DATED : July 15, 1980
INVENTOR(S) : Marcel Korn

It is certified that error appears in the above—identified patent and that said Letters Patent is hereby corrected as shown below:

Claim 1, line 32-33, delete the parenthetical phrase, "(and receive an archwire in)".

Claim 1, line 39, delete the parenthetical word, "(and)".

Signed and Sealed this

Tenth Day of March 1981

[SEAL]

Attest:

RENE D. TEGTMEYER

Attesting Officer     Acting Commissioner of Patents and Trademarks